United States Patent [19]

Imm et al.

[11] Patent Number: 5,057,632

[45] Date of Patent: Oct. 15, 1991

[54] PROCESS FOR PREPARING DINITROTOLUENE

[75] Inventors: Peter C. Imm, Sulphur; Allan B. Quakenbush, Lake Charles, both of La.

[73] Assignee: Olin Corporation, Cheshire, Conn.

[21] Appl. No.: 600,785

[22] Filed: Oct. 22, 1990

[51] Int. Cl.$^5$ .............................................. C07C 7/06
[52] U.S. Cl. ..................... 568/934; 568/939; 568/940
[58] Field of Search .................. 568/934, 939, 940

[56] References Cited

U.S. PATENT DOCUMENTS

| | | | |
|---|---|---|---|
| 1,657,723 | 1/1928 | Rodd et al. | 568/934 |
| 2,362,743 | 2/1943 | Crater | 568/934 |
| 3,928,395 | 12/1975 | Seha et al. | 568/934 |
| 3,957,889 | 5/1976 | Milligan et al. | 568/934 |
| 4,064,147 | 12/1977 | Thelen et al. | 568/934 |
| 4,367,347 | 1/1983 | Sawicki | 568/934 |
| 4,663,490 | 5/1987 | Gerken et al. | 568/934 |
| 4,804,792 | 2/1989 | Mason et al. | 568/939 |
| 4,918,250 | 4/1990 | Mason et al. | 568/934 |

FOREIGN PATENT DOCUMENTS 279312 8/1988 Fed. Rep. of Germany .

*Primary Examiner*—Robert L. Stoll
*Assistant Examiner*—Chhaya Sayala
*Attorney, Agent, or Firm*—Dale Lynn Carlson

[57] ABSTRACT

Described herein is a continuous process for preparing dinitrotoluene by reacting toluene with dilute nitric acid to produce mononitrotoluene, then reacting the mononitrotoluene with concentrated nitric acid to produce dinitrotoluene.

7 Claims, No Drawings

PROCESS FOR PREPARING DINITROTOLUENE

FIELD OF THE INVENTION

This invention relates to a continuous process for preparing dinitrotoluene by reacting toluene with dilute nitric acid to produce mononitrotoluene and then reacting the mononitrotoluene with concentrated nitric acid to produce dinitrotoluene.

BACKGROUND OF THE INVENTION

Nitration reactions of aromatic hydrocarbons are generally conducted in mixed acid systems, such as mixed nitric and sulfuric acids. However, these mixed acid systems usually involve reconcentration of the spent sulfuric acid after the nitration reaction. This reconcentration step is time consuming, energy intensive and requires the use of expensive materials of construction. In addition, the use of sulfuric acid tends to result in significant nitrocresol and cyanide by-product formation which requires expensive waste-water treatment to remove.

In view of these disadvantages associated with mixed nitric/sulfuric acid systems, there have been recent attempts to perform gas phase or liquid phase nitrations in concentrated nitric acid in the absence of sulfuric acid. By way of illustration:

U.S. Pat. No. 2,362,743 discloses a two-step process for the manufacture of dinitrotoluene ("DNT") in the absence of sulfuric acid which comprises (a) nitrating toluene to mononitrotoluene using a nitric acid having a concentration of from about 60% to about 75% and a mole ratio of toluene to nitric acid of about 1 to about 3.5 and (b) nitrating the mononitrotoluene to dinitrotoluene using nitric acid having a concentration of from about 90% to about 100%, and a mole ratio of mononitrotoluene to nitric acid of about 1 to about 3. Although the process of this patent is advantageously conducted in the absence of sulfuric acid, it was found that in step (b), a very high percentage of the nitrated product (up to 25%) based upon the amount of toluene reactant employed does not phase separate from the nitric acid medium. The patent teaches vacuum distillation of the product mixture to isolate the desired dinitrotoluene, which is an expensive and highly energy intensive process step.

U.S. Pat. No. 3,928,395 describes a process for nitrating unsubstituted or substituted benzene at a reaction temperature of −40° C. to 80° C. using 90% to 100% nitric acid in the optional and preferred presence of a dipolar aprotic solvent, wherein the reaction is halted by means of a dipolar aprotic solvent.

U.S. Pat. No. 3,957,889 describes an improved process for nitrating toluene or ortho-xylene with nitric acid, the improvement being enhancing the rate of the nitration reaction by carrying it out in the presence of at least an effective amount of anhydrous calcium sulfate or soluble anhydrite U.S. Pat. No. 4,064,147 describes the preparation of aromatic mononitro compounds (such as mononitrobenzene) by a liquid phase reaction with nitric acid having an acid concentration of between 70% and 100% by weight using a reaction temperature of between 0° C. and 80° C. When employing a relatively reactive compound such as benzene or toluene as a starting material, this patent teaches that a nitric acid concentration of between 70 and 90% by weight is preferred. The process of this patent requires a ratio of nitric acid plus water to organic components of not below 3 when using 70% nitric acid, and not below 8 when using 100% nitric acid. However, it has now been found that such a high acid ratio using 100% nitric acid tends to favor dinitro-compound production, not desired by the process of the patent.

U.S. Pat. No. 4,804,792 describes the nitration of benzene and toluene by contacting these with concentrated nitric acid in the presence of a molten nitrate salt. The patent states that the molten salt serves as a temperature regulator for the reaction and as an isothermal medium for the reactants. A preferred method of contacting the reactants in the presence of the molten salt is stated to be by bubbling the reactants into a bath of the molten salt by means of a carrier gas such as nitrogen. The vapor phase reaction is stated to be carried out at a temperature of between 150° C. and 250° C.

U.S. Pat. No. 4,918,250 describes a process for nitrating toluene to dinitrotoluene (DNT) and phase separation of the product using an inorganic salt as a phase separation agent. In this patent, DNT is produced in a two-step liquid phase nitration reaction between nitric acid and toluene in the absence of sulfuric acid and solvent. In the process of the patent, the inorganic salt is incorporated into the mixture of DNT and unreacted nitric acid in an amount sufficient to cause phase separation of the mixture in order to facilitate isolation of the DNT from the unreacted nitric acid in the product mixture (column 2, lines 27 to 33).

Since dinitrotoluene is useful as an intermediate in producing toluene diisocyanate, new processes for the selective manufacture of this intermediate would be highly desirable to the polyisocyanate manufacturing community.

DESCRIPTION OF THE INVENTION

This invention is directed to a facile continuous process for the production of dinitrotoluene. Specifically, the process of this invention comprises the following steps:

(a) reacting toluene with dilute nitric acid to produce a mixture containing mononitrotoluene, unreacted nitric acid and water;

(b) then separating the mononitrotoluene from the mixture;

(c) then reacting the mononitrotoluene recovered from step (b) with concentrated nitric acid to produce a mixture of dinitrotoluene, unreacted nitric acid and water;

(d) then separating the nitric acid from the mixture for recycle to step (c);

(e) then adding water to the mixture;

(f) then separating the dinitrotoluene from the mixture; and (g) then recycling the dilute nitric acid from step (f) to step (a).

The continuous process of this invention provides a facile continuous process for preparing dinitrotoluene. The process of this invention does not require the use of sulfuric acid, solvent or similar materials.

In the process of this invention, toluene is reacted with dilute nitric acid (an acid concentration of about 75 weight percent) at a temperature of about 35° C. to about 70° C., preferably from about 40° C. to about 50° C. to produce a mixture of mononitrotoluene, water and unreacted nitric acid. Excess nitric acid may be added to the reaction to drive the nitration reaction to completion.

The reaction may be carried out in a single reactor or series of reactors to achieve the proper efficiency. The reaction is heterogeneous so the reactor(s) is generally agitated to enhance the reaction rate. Thus, a stirred tank reactor is preferred.

The molar ratio of dilute nitric acid to toluene employed in the reaction is generally between about 5:1 to about 7:1, preferably between about 6:1 to about 7:1. The reaction is generally conducted at atmospheric pressure, although upper and lower pressures may be employed, if desired. The reaction time is typically less than about 4 hours, preferably less than about 1 hour.

The mononitrotoluene thus produced is then separated from its mixture with unreacted nitric acid and water. This separation can be accomplished by simply allowing the mixture to settle in, for example, a phase separator, and then decanting the mononitrotoluene, since two phases are formed, an organic phase containing the mononitrotoluene and an aqueous phase containing the nitric acid and water. Other known separating means can may be used to separate the mononitrotoluene from the reaction mixture.

The mononitrotoluene thus separated may then be recycled to the dinitration reactor(s) where it is reacted with concentrated nitric acid.

Water is then removed from the aqueous phase containing dilute nitric acid and water by, for example, distillation means leaving dilute nitric acid which may be recycled to the mononitration reactor for reaction with toluene under the conditions as previously discussed.

The mononitrotoluene thus produced and separated in the first step is then reacted with concentrated nitric acid (an acid concentration of between 95 and 100 weight percent, preferably at least 98 weight percent) in a dinitration reactor(s). The reaction is carried out at a temperature of from about 40° C. to about 80° C., preferably from about 70° C. to about to 80° C., to produce a mixture of dinitrotoluene, water and unreacted nitric acid.

The molar ratio of concentrated nitric acid to mononitrotoluene employed in the reaction is generally between about 4:1 and about 12:1, preferably between about 5:1 and about 9:1.

The reaction is generally conducted at atmospheric pressure, although higher and lower pressure can be employed, if desired. The reaction time is typically less than about 8 hours, preferably less than about 2 hours.

The product mixture containing dinitrotoluene, water and unreacted nitric acid is then distilled to remove nitric acid which is recycled to the dinitration reactor for subsequent reaction with mononitrotoluene.

The remaining product mixture is then removed from the distillation column, water added and dinitrotoluene separated out in, for example, a crystallizer. The dilute nitric acid remaining is then recycled to the mononitration reactor(s) for subsequent reaction with toluene.

EXAMPLE

The following example serves to give specific illustration of the practice of this invention, but is is not intended in any way to limit the scope of this invention.

EXAMPLE 1

Dinitrotoluenene (26.1 grams) was dissolved into 75% nitric acid (100 grams) at 40° C. When the solution was cooled to 1° C., 8.8 grams of DNT were crystallized from solution. This left 17.3 grams of DNT in the 75% acid. In a second experiment, DNT (34.0 grams) was dissolved into 70% nitric acid (100 grams) at 41° C. When the solution temperature was dropped to 1° C., 26.8 grams of DNT were crystallized from solution. This left 7.2 grams of DNT in the 70% acid which was less than half of dissolved DNT in the 75% acid. These measurements demonstrated the ability to crystallize DNT from nitric acid solutions. They also showed the sensitivity of DNT solubility in dilute nitric acid to small changes in water concentration.

While the invention has been described above with reference to specific embodiments thereof, it is apparent that many changes, modifications, and variations can be made without departing from the inventive concept disclosed herein. Accordingly, it is intended to embrace all such changes, modifications, and variations that falls within the spirit and broad scope of the appended claims. All patent applications, patents, and other publications cited herein are incorporated by reference in their entirety.

What is claimed is:

1. A continuous process for the production of dinitrotoluene comprising the following steps:
   (a) reacting toluene with dilute nitric acid to produce a product mixture containing mononitrotoluene, water and unreacted nitric acid;
   (b) then separating the mononitrotoluene from the mixture;
   (c) then reacting the mononitrotoluene recovered from step (b) with concentrated nitric acid to produce a product mixture containing dinitrotoluene, water and unreacted nitric acid;
   (d) then separating a portion of the nitric acid from the mixture for recycle to step (c);
   (e) then adding water to the mixture of water, unreacted nitric acid and dinitrotoluene;
   (f) then separating the dinitrotoluene from the mixture by crystallization;
   (g) then recycling the remaining dilute nitric acid from step (f) to step (a).

2. A process as defined in claim 1, wherein step (a) is carried out at a temperature of from about 35° C. to about 70° C.

3. A process as defined in claim 1, wherein the molar ratio of dilute nitric acid to toluene in step (a) is between about 5:1 and about 7:1.

4. A process as defined in claim 1, wherein the nitric acid in step (a) is at a concentration of about 75 weight percent.

5. A process as defined in claim 1, wherein step (c) is carried out at a temperature of from about 40° C. to about 80° C.

6. A process as defined in claim 1, wherein the nitric acid in step (c) is at a concentration of between 95 and 100 weight percent.

7. A process as defined in claim 1, wherein the molar ratio of concentrated nitric acid to mononitrotoluene in step (c) is between about 4:1 and about 12:1.

* * * * *